(12) United States Patent
Bell

(10) Patent No.: US 6,247,211 B1
(45) Date of Patent: Jun. 19, 2001

(54) MEDICAL TUBING TETHERING DEVICE

(75) Inventor: Craig J. Bell, East Swanzey, NH (US)

(73) Assignee: MedCare Medical Group, Inc., East Swanzey, NH (US)

( * ) Notice: Subject to any disclaimer, the term of this patent is extended or adjusted under 35 U.S.C. 154(b) by 0 days.

(21) Appl. No.: 09/437,849

(22) Filed: Nov. 10, 1999

(51) Int. Cl.$^7$ .................................................. A44B 21/00
(52) U.S. Cl. ........................... 24/306; 24/298; 604/179
(58) Field of Search ........................... 24/298–304, 306, 24/442, 3.11, 3.12, 3.13; 604/174, 179; 128/DIG. 26; 248/317, 74.2, 74.4

(56) References Cited

U.S. PATENT DOCUMENTS

| | | | | |
|---|---|---|---|---|
| 4,074,397 | * | 2/1978 | Rosin ........................... 128/DIG. 26 |
| 4,308,642 | * | 1/1982 | Heyman ................................. 24/306 |
| 4,639,980 | * | 2/1987 | Peterson ................................. 24/306 |
| 4,707,906 | * | 11/1987 | Posey ................................. 24/298 X |
| 5,704,916 | * | 1/1998 | Byrd ...................................... 604/179 |
| 5,709,665 | * | 1/1998 | Vergano et al. ...................... 604/174 |
| 5,774,950 | * | 7/1998 | Stout ...................................... 24/306 |
| 5,879,335 | * | 3/1999 | Martinez et al. ..................... 604/179 |

* cited by examiner

Primary Examiner—Robert J. Sandy
(74) Attorney, Agent, or Firm—Davis & Bujold, P.L.L.C.

(57) ABSTRACT

A medical tubing tethering device comprising a tether having a first proximal end and an opposed distal end. A first mechanism is supported adjacent the proximal end of the tether for securing the medical tubing tethering device to a desired object. The distal end of the tether has a second attachment mechanism for coupling a medical tube thereto to facilitate support of the medical tube once the medical tubing tethering device is supported by the desired object. The tether can be substantially helical so as to be capable of wrapping around the medical tube to tether the medical tube to the patient to prevent unwanted movement of the medical tube relative to the patient. The tether may also be a flexible strap with a pressure sensitive adhesive or a hook and loop touch fastener. The medical tubing tethering device can also be used in combination with a stand alone anchor to facilitate use with a wider range of coupling surfaces.

20 Claims, 6 Drawing Sheets

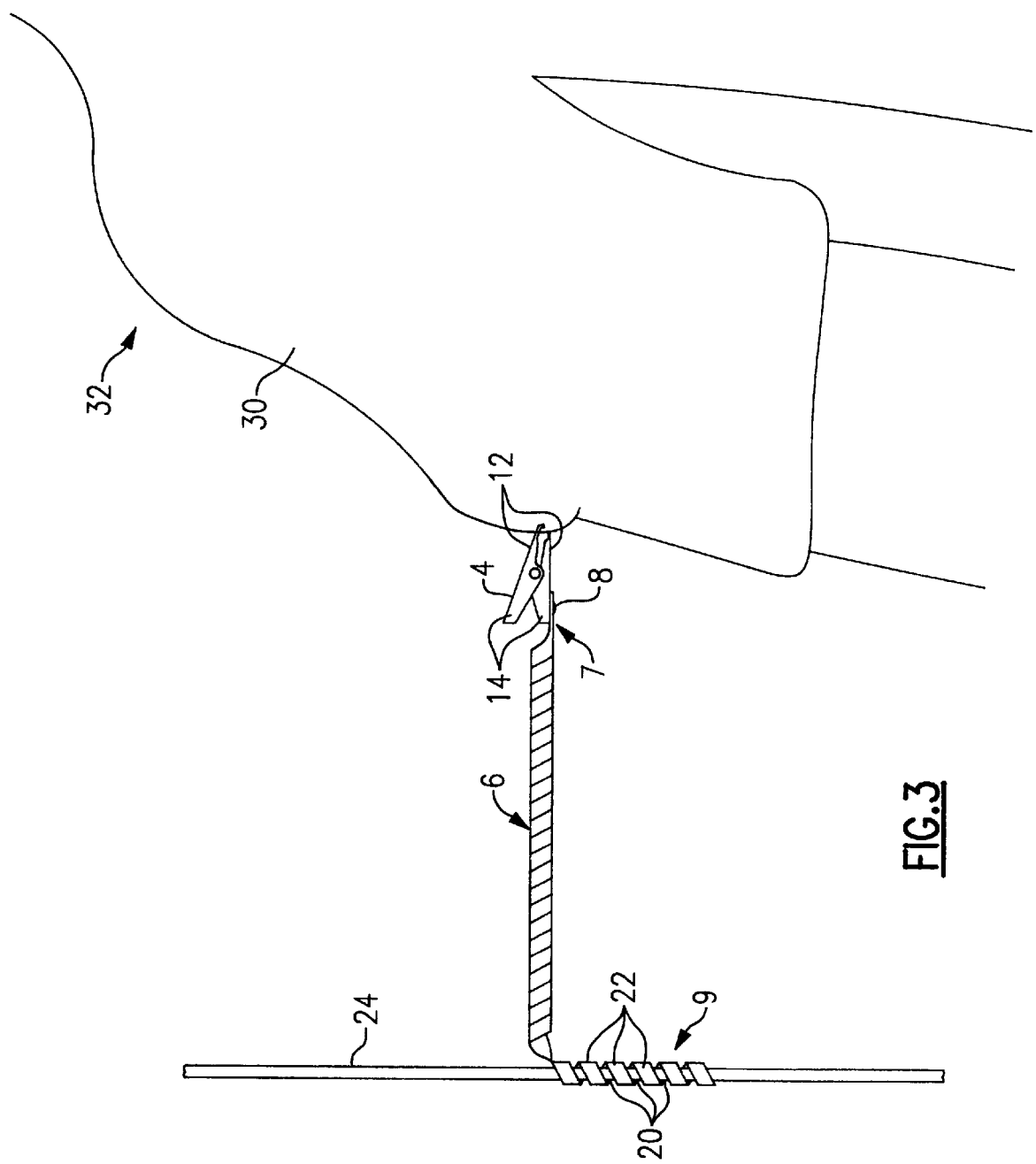

MEDICAL TUBING TETHERING DEVICE

FIELD OF THE INVENTION

The present invention relates generally to a new medical tubing tethering device that provides a mechanism for easily and safely tethering a medical tubing and/or a catheter to the patient. This new medical tubing tethering device minimizes any direct pulling force on a supported catheter or the medical tubing that may result from either the patient or the equipment moving.

BACKGROUND OF THE INVENTION

In the field of medicine and in the treatment of patients, access to the body's vascular system is imperative. The vascular system is generally accessed in a conventional way, such as a hypodermic needle or a catheter. These devices are avenues to monitor certain physiological parameters, to sample blood for analysis, to infuse replacement blood/fluids, and to deliver medications. Whatever the reason and for what ever the duration the access is required, inadvertent removal or dislodgement of the access coupling can effect treatment efficacy and compromise the patient's condition.

Typically access is provided by a winged infusion needle or a catheter being placed in a blood vessel and then taped to the patient's skin to anchor the exit site of the winged infusion needle or the catheter. The extension tubing, of the winged infusion needle or the catheter, is then looped and taped at another adjacent site to the patient's arm or to an arm board. In addition to this, clinical practice calls for a piece of tape to be placed around the intravenous medical tubing so it adheres back onto itself. A safety pin is then used to puncture and clip both an end portion of the tape and an adjacent portion of the patient's clothing to secured those to components to one another. Such connection keeps the intravenous medical tubing from pulling directly on the catheter/needle connection and/or the exit site. Pulling primarily results from movement of the patient, although it can occur when clinicians are manipulating equipment during treatment and/or repositioning of the patient.

It is a primary concern to eliminate the above mentioned tape and safety pin method from current practice because it poses a potential for a sharps injury to either, or both, the patient and/or care giver, e.g the safety pin has the potential for injuring the patient when it is placed and also could stick the care giver. This results in a potential for cross-contamination and infection of either, or both, the patient and care giver. With respect to pediatric applications, a child may possibly open the safety pin and get stuck or stick an unsuspecting care giver.

SUMMARY OF THE INVENTION

Wherefore, it is an object of the present invention to overcome the aforementioned problems and drawbacks associated with the prior art devices and methods.

The medical tubing tethering device, according to the present invention, relates to tethering a vascular system access device and/or the fluid delivery tubing that connects to the access device and to the patient in order to prevent inadvertent dislodgement or removal of the vascular system access device and/or the fluid delivery tubing.

The invention, in its simplest form, provides a first attachment means for attaching to either the patient, the patient's clothing, or some other patient related support apparatus and a second attachment means for attaching to at least one tube, such as an extension tube, a catheter, etc.

In a preferred embodiment, the invention consists of a coil or helix member that can be wrapped around an intermediate section of the medical tubing as the second attachment means. The helix is connected to a clamp or clip (the first attachment means) that can safely and easily attach to the patient's clothing. The expandable characteristics of the helix member allows it to be wrapped around one or more tubing lines. The medical tubing tethering device can be economically constructed from a plastic material and/or metals or other known materials.

Another embodiment is constructed of a strip off flexible plastic or fabric with pressure sensitive adhesive on at least one side of the flexible plastic tether. The strip of flexible plastic is permanently connected to a clamp or clip for attachment to the patient's clothing. A release liner is peelable from the adhesive and the flexible plastic strip is then wrapped or wound around one or more medical tubings to provide the second attachment means.

The third and fourth embodiments both utilize a strip of flexible material carrying a hook or a loop fastener, on at least one surface thereof, for connection to the medical tubing. The opposite end of the strip of flexible material can be attached to the patient's clothing with a clip (the third embodiment) or additional hook and loop fasteners (the fourth embodiment).

If desired, the clip for each of the above embodiments, of the present invention, can incorporate a locking mechanism that would prevent curious patients, e.g. children, from removing or repositioning the clip without clinical assistance.

A further enhancement to the medical tubing tethering device is an associated stand alone anchor member. If a conventional attachment to the patient's clothing is unacceptable for a particular application, then the stand alone anchor attachment is preferred. This anchor attachment comprises a piece of plastic, fabric or like material with a pressure sensitive adhesive base surface. This base surface is adhered at an appropriate anchor location for the patient and the medical tubing tethering device is then attached to the anchor member via the first attachment means. In another embodiment of the anchor member, the anchor is a strip of material with associated hook and loop fasteners which are wrapped around an appendage or other apparatus and secured in a conventional manner.

These and further objects and features of the present invention will become apparent to those skilled in the art to which this invention pertains and with referenced to the following disclosure and the appended claims.

BRIEF DESCRIPTION OF THE DRAWINGS

The invention will now be described, by way of example, with reference to the accompanying drawings in which:

FIG. 3 diagrammatically shows the clip attached to the patient's clothing and the helical tube attached to the medical tubing to provide support for the medical tubing;

DETAILED DESCRIPTION OF THE INVENTION

Briefly described, the present invention relates to a new medical tubing tethering device that provides a mechanism for easily and safely tethering a one or more medical tubings and/or catheters to the patient. The medical tubing tethering device is an improvement over the prior art in that it is relatively simple to use, is cost effective, and essentially eliminates the possibility of a sharps injury to either the patient and/or the care giver. The following description is of four preferred embodiments of the present invention and is in no way meant to limit the scope of the present invention, the size or shape of the medical tubing tethering device, the type of materials used for construction of the medical tubing tethering device or the arrangement or orientation of the various components of the medical tubing tethering device.

Figure 1A:
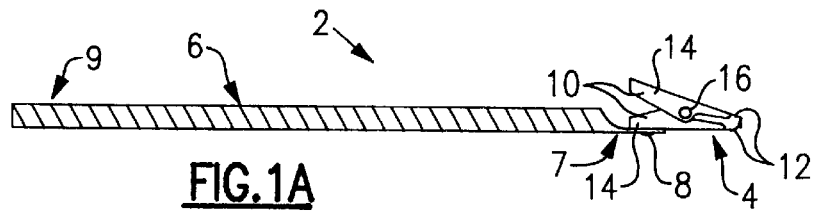
FIG. 1A illustrates a diagrammatic side elevational view of the present invention.

Referring first to FIG. 1A, the medical tubing tethering device 2, according to the present invention, is generally shown. It comprises a first attachment means such as a conventional clamp or clip 4, e.g. a standard alligator clip, and a second attachment means such as a generally elongate tether or helical tube 6. A conventional coupling means or mechanism 8 interconnects a free end portion of the clamp or clip 4 with a leading end of the helical tube 6 to permanently couple those two members with one another.

The clip 4 generally comprises a pair of elongate mating members 10 which each have a clamping jaw 12 formed at one end and a handle 14 formed at a remote end thereof. Both of the mating members 10 are pivotally attached to one another, at an intermediate portion thereof designated as element 16, to allow limited relative pivoting movement between the two mating members 10. An internal spring (not shown in detail), biases the two handles 14 away from one another so that the two opposed clamping jaws 12 are brought into contact with one another to facilitate sandwiching a desired component or item therebetween. The clip 4 is normally biased into a closed clamping position by the spring). As such clips are conventional and well known in the art, a further detailed description concerning the same is not provided.

The conventional coupling means or mechanism 8, which interconnects the end portion of the clamp or clip 4 with the leading proximal end portion 7 of the helical tube 6, can be, for example, a conventional nut and bolt combination, glue or some other common adhesive, a clamping arrangement, a crimping arrangement or some other known attachment arrangement for permanently attaching the leading edge of the helical tube 6 to the clip 4. As such attachment arrangements are conventional and well known in the art, a further detailed description concerning the same is not provided.

The helical tube 6 can be manufactured by either helically cutting a tubular material at a desired helix angle (e.g an angle of between 5 degrees and 80 degrees and, more preferably, an angle of between 45 degrees and 65 degrees), wrapping a flat stock material around a mandrel and suitably heating the wrapped stock material to impart a helix memory thereto, or by any other conventional and well known manufacturing processes.

Figure 1B:
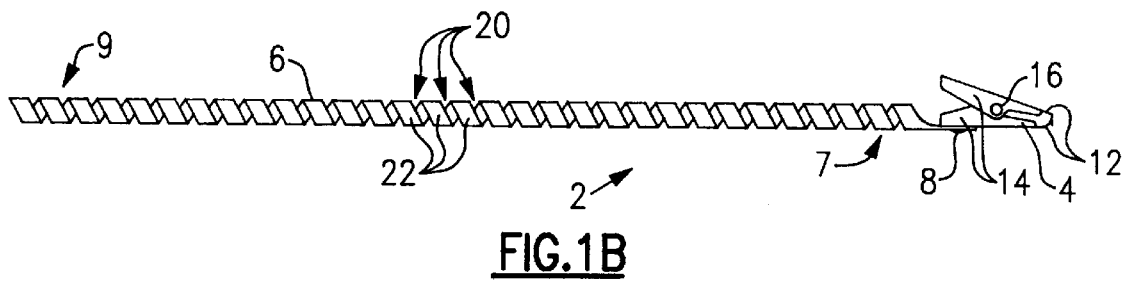
FIG. 1B illustrates a diagrammatic side elevational view of the present invention, similar to that of FIG. 1A, with the helical tube being shown in its partially stretched orientation.
Figure 2A:
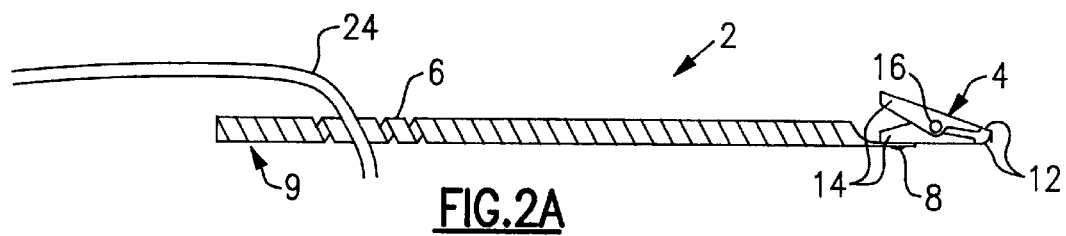
FIG. 2A diagrammatically illustrates a medical tubing being initially inserted in a gap formed between adjacent wraps of the helical tube.
Figure 2B:
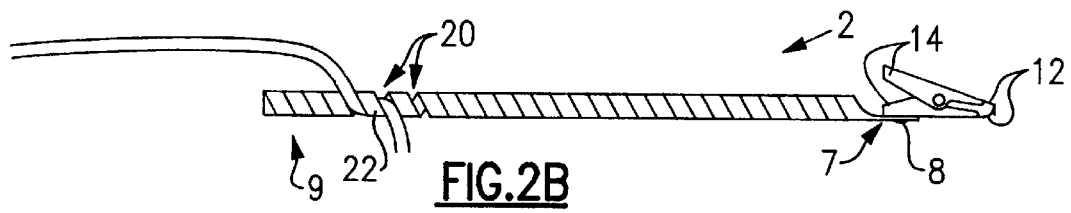
FIG. 2B diagrammatically illustrates the medical tubing of FIG. 2 being by one wrap of the helical tube.
Figure 2C:
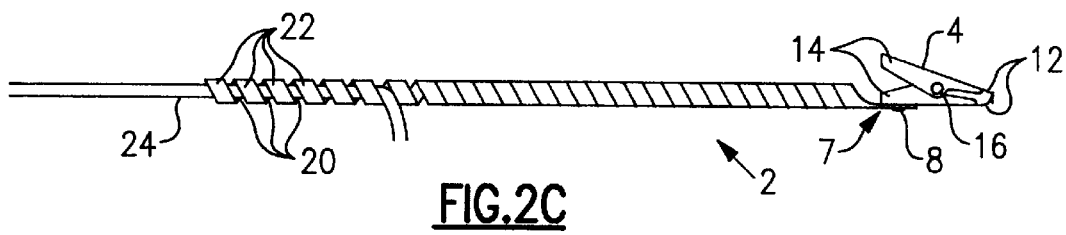
FIG. 2C diagrammatically illustrates the medical tubing of FIG. 2 being by several wraps of the helical tube.

As can be seen in FIG. 1B the helical tube 6 comprises a generally elongate flat member which has a generally helical configuration and a plurality of equally spaced gaps 20 formed between each adjacent pair of wraps 22 when the helical tube 6 is expanded or stretched, as can be seen in FIG. 1B. When use of the medical tubing tethering device 2, to support a desired medical tubing 24 is required, the distal end of the helical tube 6 is pulled or otherwise at least partially expanded to facilitate placing the medical tubing 24 between a desired gap 20 formed between two adjacent wraps 22 of the helical tube 6. Once this has occurred, the care giver can then wraps the distal end portion 9 of the helical tube 6 and the medical tube 24 to facilitate wrapping of the helical tube 6 a sufficient amount of times around the medical tube 24 so that each additional wrap of the helical tube 6 encases and surrounds the medical tubing 24, as can be seen in FIG. 2C.

Once such wrapping is achieved, the medical tubing 24 is substantially supported by the distal end portion 9 of the helical tube 6 due to the inherent resiliency of the helical tube 6. Next, the care giver will squeeze the two handles 14 of the clip 4 to open the clamping jaws 12 a sufficient amount to facilitate clamping, via the clamping jaws 12, to a desired piece of clothing 30 or a patient 32 or some other article. Thereafter, the care giver releases the two handles 14 of the clip 4 so that the clamping jaws 12 sandwich the clothing 30 therebetween, as can be seen in FIG. 3, for example.

Due to this arrangement, the medical tubing 24 is now supported by the medical tubing tethering device 2 and the helical tube 6 inherently provides a springing or clamping effect, due to is normally smaller interior diameter. The helical tube 6 has an interior diameter of between $\frac{1}{32}$ and 1.0 inches and, more preferably, an interior diameter of between $\frac{1}{8}$ and $\frac{3}{8}$ inches and a helix angle of between 5 degrees and 80 degrees and, more preferably, a helix angle of between 45 degrees and 65 degrees. The medical tubing tethering device 2 allows the medical tubing 24 to have limited movement relative to the clip 4 while still being retained.

Figure 4:
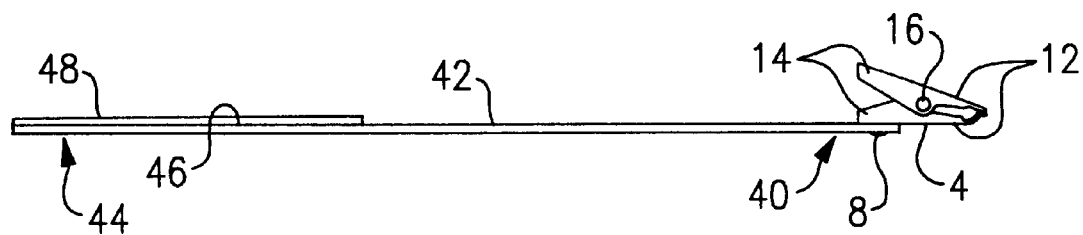
FIG. 4 diagrammatically illustrates a second embodiment of the present invention shown with a plastic strap and accompanying adhesive layer.
Figure 5:
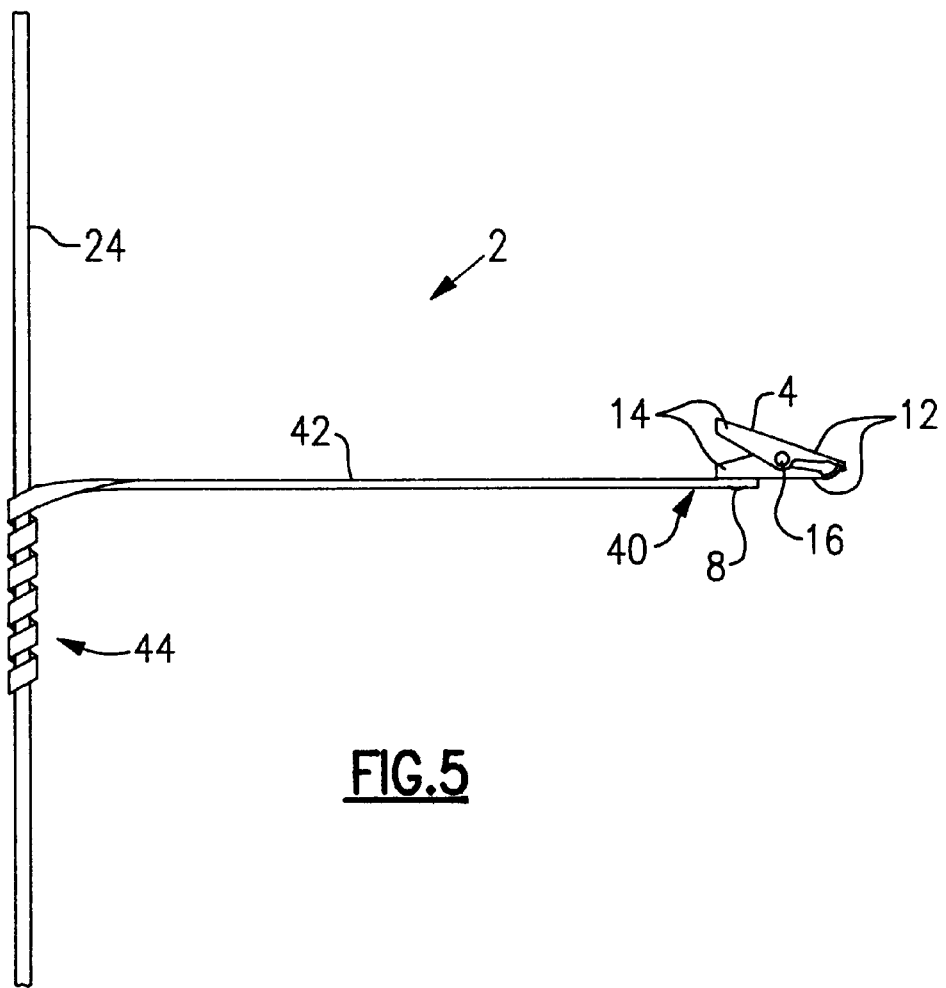
FIG. 5 diagrammatically illustrates attachment of plastic strap and accompanying adhesive layer, according to the embodiment of FIG. 4, to a to medical tubing.

With reference to FIGS. 4 and 5, a detailed description concerning a second embodiment of the present invention will now be provided. As this embodiment is very similar to the first embodiment, only the variations between this embodiment and the first embodiment will be discussed in detail. As with the previous embodiment, a clip 4 is provided as the first attachment means. A proximal end 40 of a plastic or fabric strap tether 42 is secured to a handle 14 of the clip 4 via in a conventional coupling means or mechanism 8. According to this embodiment, the plastic or fabric strap tether 42 is a generally flexible planar member which has a length dimension of about 6 inches and width dimension of about ¼ of an inch and a thickness of about 1/32 of an inch. At least one surface of a distal end 44 portion of the plastic strap tether 42 carries a pressure sensitive adhesive 46, such as a Minnesota Mining and Manufacturing (3M) acrylic adhesive. A protective liner 48 covers and protective the adhesive 46 until use of the medical tubing tethering device 2 is desired.

When use is required, a care giver will peel back the protective liner 48 from the plastic strap tether 42 to expose the underlying adhesive 46. Once this has occurred, the care giver can then commence wrapping the plastic strap tether 42, such that the adhesive 46 will be facing toward and engage with an exterior surface of the medical tubing 24, as can be seen in FIG. 5. The care giver will wrap the plastic strap tether 42 around the exterior circumference of the medical tubing 24 a desired number of times, e.g. between 3–15 wraps for example, to facilitate a substantially permanent attachment of the medical tubing 24 to the distal end 44 of the plastic strap tether 42. Alternatively, it is to be appreciated that the plastic strap tether 42 can be wrapped around the exterior circumference of the medical tubing 24, at least once, and then engaged back with its so that the two surfaces carrying the adhesive 46 engage with one another to secure the plastic strap tether 42 to the medical tubing 24. Next, the care giver then clamps the clip 4 to a desired piece of clothing of the patient (not shown) or to some other article or component to facilitate suspending the medical tubing 24 in a desired orientation relative to the clip 4.

Figure 6:
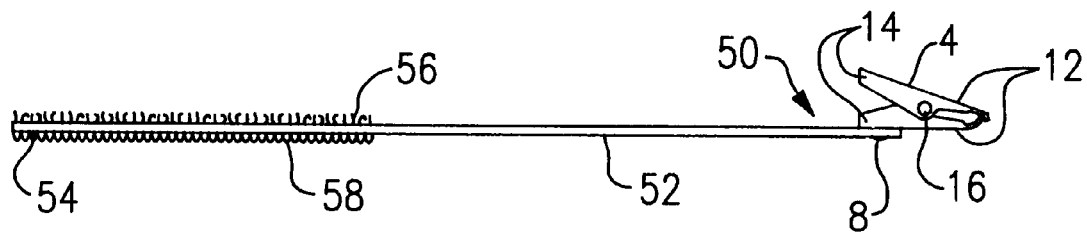
FIG. 6 diagrammatically illustrates a third embodiment of the present invention shown with mating hook and loop touch fasteners.
Figure 7:
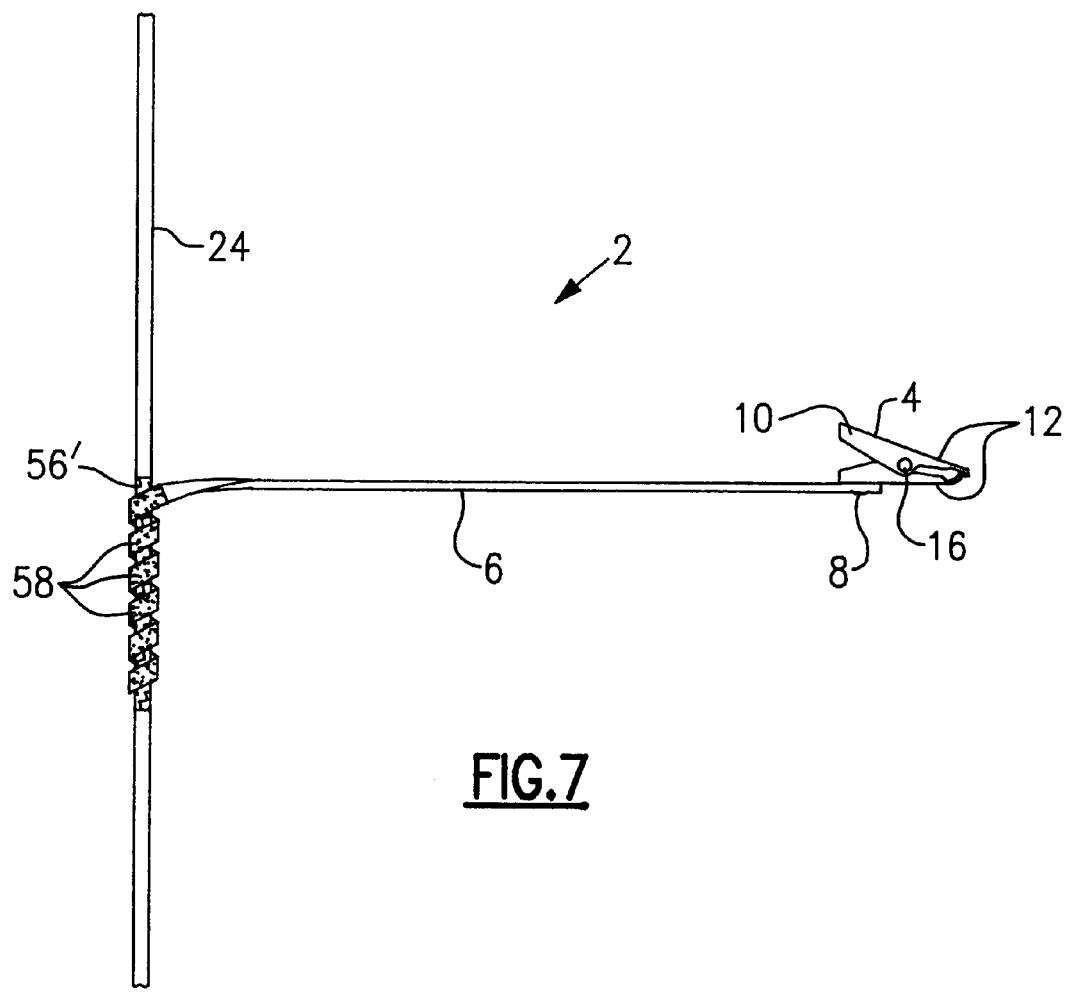
FIG. 7 diagrammatically illustrates attachment of plastic strap and accompanying hook or loop touch fastener, according to the embodiment of FIG. 6, to a mating loop or hook touch fastener of the medical tubing.

With reference to FIGS. 6 and 7, a detailed description concerning a third embodiment of the present invention will now be provided. As this embodiment is somewhat similar to the previous embodiments, only the variations between this embodiment and the other embodiments will be discussed in detail. As with the second embodiment, a conventional clip 4 is provided as the first attachment means. A proximal end portion 50 of a plastic strap tether 52 is secured to a handle 14 of the clip 4 via in a conventional coupling means or mechanism 8.

According to this embodiment, the plastic strap tether 52 is a generally flexible planar member which has a length dimension of about 6 inches and width dimension of about ¼ of an inch and a thickness of about 1/32 of an inch. At least one surface of said plastic strap tether 52, and possibly both opposed surfaces adjacent the distal end 54, carry at least one of a mating hook and loop touch fastener. As seen in FIG. 6, for example, a first surface of the distal end 54 of the plastic strap tether 52 is provided with a hook touch fastener 56 while the second opposed surface, of the distal end 54 of the plastic strap tether 52, is provided with a mating loop touch fastener 58.

An intermediate portion of the medical tubing 24 is provided with a mating hook and loop touch fastener 56' or 58' so that when the mating touch fastener 56 or 58 of the plastic strap tether 52 is brought into engagement with the hook or loop touch fastener of the medical tubing 24, the medical tubing 24 is releasably supported by the distal end portion 54 of the plastic strap tether 52, as can be seen in FIG. 7.

Figure 8:
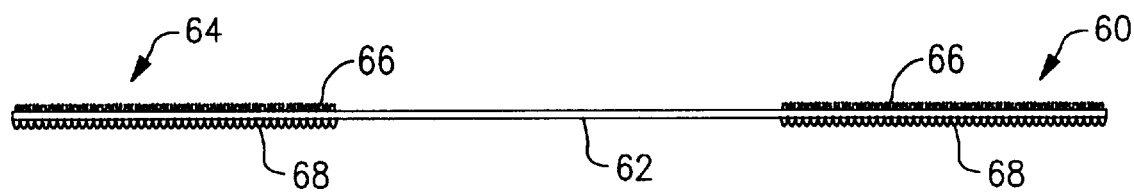
FIG. 8 diagrammatically illustrates a fourth embodiment of the present invention shown with mating hook and loop touch fasteners for both the first and second attachment means.
Figure 9:
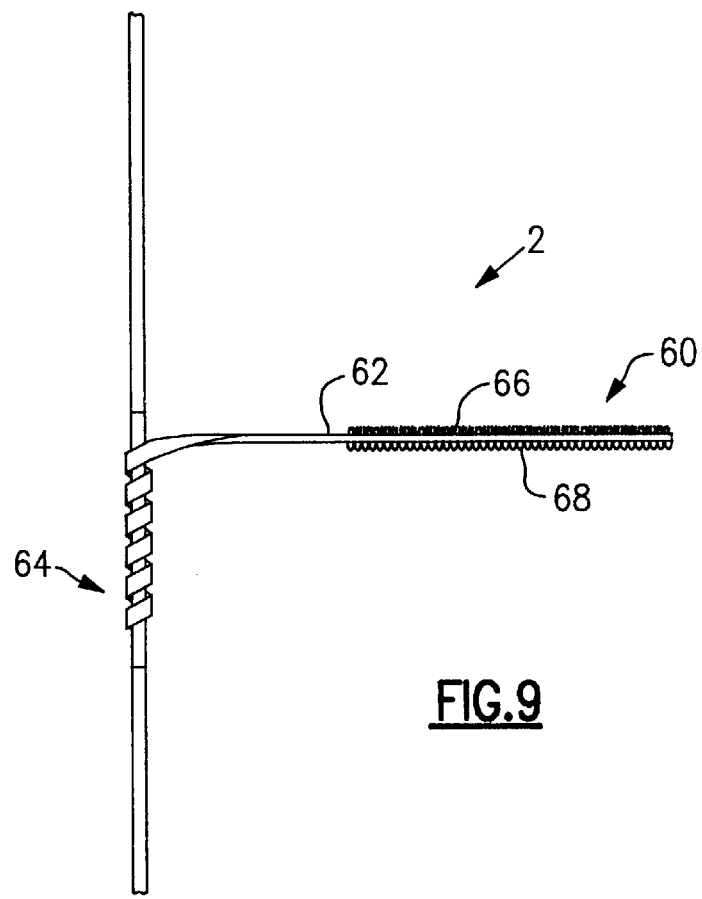
FIG. 9 diagrammatically illustrates attachment of plastic strap and accompanying hook or loop touch fastener, according to the embodiment of FIG. 8, to a mating loop or hook touch fastener of the medical tubing and on a desired article.

With reference to FIGS. 8 and 9, a detailed description concerning a fourth embodiment of the present invention will now be provided. As this embodiment is somewhat similar to the third embodiment, only the variations between this embodiment and the third embodiment will be discussed in detail. According to this embodiment, the clip is eliminated and both the proximal end portion 60 and the distal end portion 64 of the plastic strap tether 62 are each provided with at least one component of a hook touch fastener 66 or loop touch fastener 68. As can be seen in FIG. 8, for example, both the distal end portion 60 and the proximal end portion 64 of the plastic strap tether 62 carry at least one component of a hook and loop touch fastener 66, 68.

As can be seen in FIG. 8, both the proximal end portion 60 and the distal end portion 64 of the first surface of the plastic strap tether 62 carries a hook component 66 of the touch fastener while both the proximal end portion 60 and the distal end portion 64 of the opposed second surface of the plastic strap tether 62 carries a loop component 68 of the touch fastener. As with the embodiment of FIG. 3, an intermediate portion of the medical tubing carries a mating hook and loop touch fastener component to facilitate engagement with one of the first and second surfaces of the distal end portion 64 of the plastic strap tether 62. To facilitate attachment of the proximal end portion 60 to the patient, a small portable flexible member 70 carrying a mating hook or loop touch fastener component 72 on a first surface thereof 74 and carrying a conventional pressure sensitive adhesive 76 on an opposed rear surface thereof 78 is provided. A release liner 80 covers the pressure sensitive adhesive 76.

When attachment is desired, a care giver peels the release liner 80 away to expose the underlying adhesive 76. Next, the portable flexible member 70 is adhesively affixed to a desired object or item, via the adhesive 76, with the mating hook or loop touch fastener component 72 facing outwardly. Lastly, either the hook component 66 carried by the first surface of the proximal end portion 60 of the plastic strap tether 62 or the loop component 68 carried by the first surface of the proximal end portion 60 of the plastic strap tether 62 is engaged with the mating hook or loop touch fastener component 72 to secured the medical tubing tethering device 2 to a desired object or surface.

According to this embodiment, the plastic strap 62 is a generally flexible planar member which has a length dimension of about 6 inches and width dimension of about ¼ of an inch and a thickness of about 1/32 of an inch.

Figure 10:
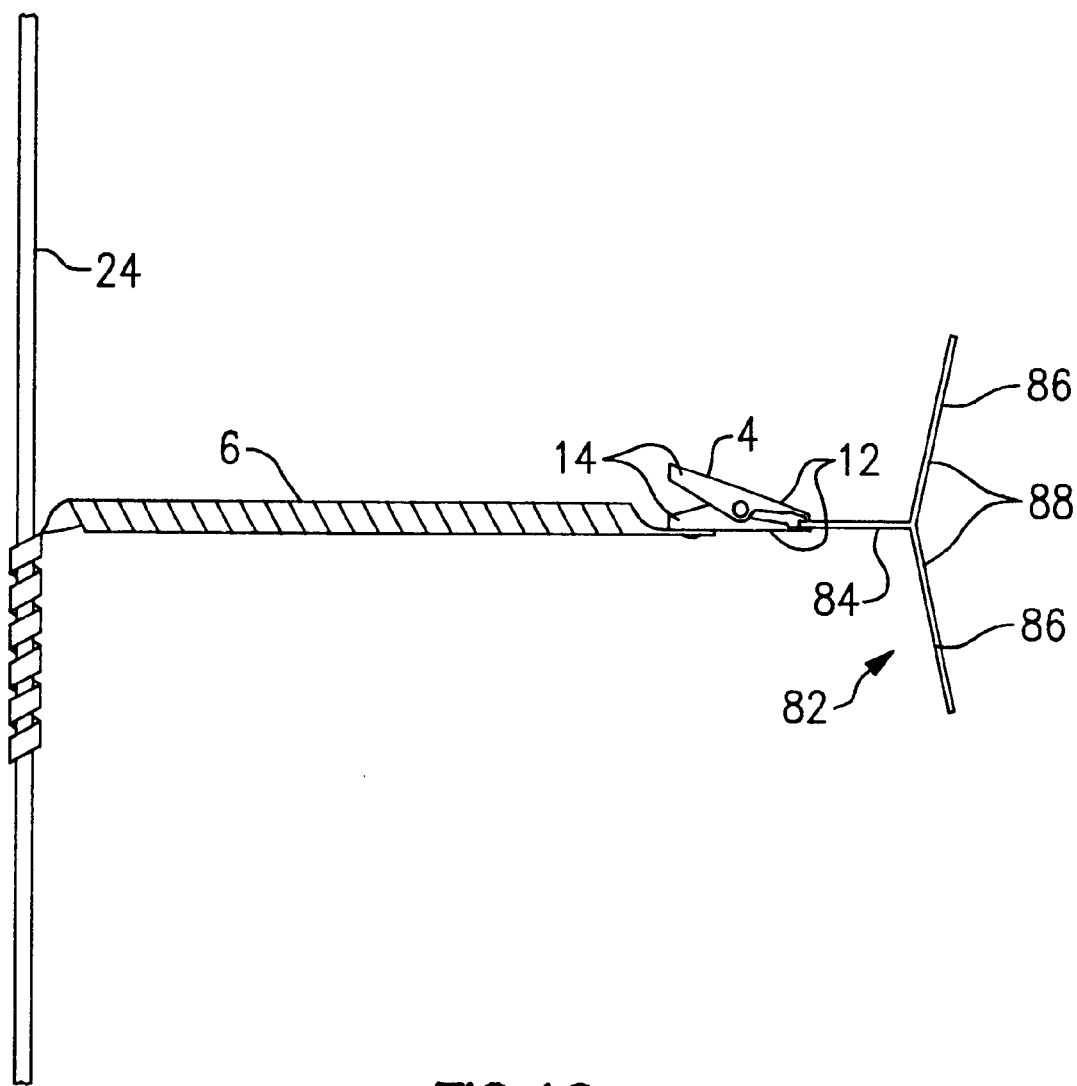
FIG. 10 diagrammatically shows the present invention spirally attached to a medical tubing and clamp attached to a stand alone anchor point.

With reference to FIG. 10, the use of the present invention in combination with a stand-alone anchor 82 can be seen. The stand-alone anchor 82 is anchor is a substantially flexible Y-shaped member which is made from a plastic material, such as polyvinylchloride, polyethylene or polystyrene, and is provided with an attachment tab 84 and at least one or preferably two surfaces 86, opposite the attachment tab 84, each contain a pressure sensitive adhesive 88 for facilitating support of the stand-alone anchor 82 on a desired object or surface. The at least one surface of the stand-alone anchor 82 is utilized to adhesively secure to stand-alone anchor 82 to either the patient's skin, a medical dressing, a part of a medical bed, a surface of associated equipment or some other object in the proximity of the patient. Thereafter, the clip 4 can be secured to the attachment tab 84 to facilitate attachment of the medical tubing tethering device 2, according to the present invention, to virtually any desired object.

The tether is preferably manufactured from a plastic material, such as polypropylene, polyethylene, polyvinylchloride, or the like. The clip can be constructed from a durable material such of a metal, e.g. stainless steel, or from a plastic material, e.g. polycarbonate.

It is to be appreciated that other conventional and well known attachment means are possible as would be apparent to those skilled in this arr. Accordingly, since certain changes may be made in the above described medical tubing tethering device and associated method, without departing from the spirit and scope of the invention herein involved, it is intended that all of the subject matter of the above description or shown in the accompanying drawings shall be interpreted merely as examples illustrating the inventive concept herein and shall not be constructed as limiting the invention.

What is claimed is:

1. A medical tubing tethering device comprising:

a tether having a proximal end and an opposed distal end;

a first attachment mechanism being supported adjacent the proximal end of the tether for securing the medical tubing tethering device to a desired object;

the distal end portion of the tether comprising a substantially helically shaped configuration, the substantially helically shaped configuration having an inherent resiliency which maintains the distal end portion of the tether in its substantially helically shaped configuration, and the inherent resiliency of the distal end portion of the tether facilitates wrapping a portion of the substantially helically shaped configuration about a circumference of a medical tube to facilitate releaseable attachment of the medical tube to the distal end portion of the tether.

2. The medical tubing tethering device according to claim 1, wherein the substantially helically shaped configuration of the distal end portion of the tether has a first static diameter and a second expanded diameter which is larger than the first diameter, and the second expanded diameter exerts a compressive retention force against the medical tube and facilitates retention of the medical tube solely via use of the medical tubing tethering device.

3. The medical tubing tethering device according to claim 1, wherein a gap is formed between each pair of adjacent wraps of the substantially helically shaped configuration of the distal end portion of the tether, and the gaps are equally spaced along the substantially helically shaped configuration of the distal end portion of the tether.

4. The medical tubing tethering device according to claim 3, wherein inherent resiliency of a plurality of wraps of the substantially helically shaped configuration of the distal end portion of the tether facilitates accommodation of the medical tube by at least one of the gaps formed between an pair of adjacent wraps.

5. The medical tubing tethering device according to claim 1, wherein the substantially helically shaped configuration of the distal end portion of the tether has a diameter which is smaller than an exterior diameter of the medical tube to be supported to provide a compressive retention force to the medical tube and facilitate retention thereof solely via use of the medical tubing tethering device; and a gap is formed between each pair of adjacent wraps of the substantially helically shaped configuration of the distal end portion of the tether, and the gaps are equally spaced along the substantially helically shaped configuration of the distal end portion of the tether.

6. The medical tubing tethering device according to claim 1, wherein the first attachment mechanism is a spring biased clip supported adjacent the proximal end portion of the tether, and the spring biased clip is spring biased into a closed clamping position.

7. The medical tubing tethering device according to claim 1, wherein the spring biased clip is manufactured from stainless steel and the tether is manufactured from a plastic material.

8. The medical tubing tethering device according to claim 1, wherein the substantially helically shaped configuration of the tether is manufactured from one of polypropylene, polyethylene, polyvinyl chloride.

9. The medical tubing tethering device according to claim 1, wherein the substantially helically shaped configuration of the tether is formed from a strip of elastic material having an adhesive layer secured to an inwardly facing surface of the strip of elastic material to facilitate adhesive support of the medical tube to the tether.

10. The medical tubing tethering device according to claim 9, wherein a release liner covers the adhesive layer and the release liner is removable to expose the adhesive layer for securing the tether to the medical tubing.

11. A medical tubing tethering device comprising:

a tether having a first proximal end and an opposed distal end;

a first attachment mechanism being supported adjacent the proximal end of the tether for securing the medical tubing tethering device to a desired object;

the distal end of the tether having a second attachment mechanism for engaging a medical tube to facilitate support of the medical tube once the medical tubing tethering device is supported by the desired object;

wherein the second attachment mechanism comprises at least one component of a mating touch fastener supported by a surface of the tether and the medical tube is provided with a mating touch fastener to facilitate securing of the distal end of the tether to the medical tube; and the first attachment mechanism comprises a first portion of a touch fastener, supported by at least one surface of the tether adjacent the proximal end portion thereof and the touch fastener is engageable with a mating touch fastener to support by the desired object.

12. The medical tubing tethering device according to claim 11, wherein a first portion of the touch fastener carried by the proximal end of the tether is used in combination with a portable mating touch fastener which has an adhesive on a rear surface thereof to facilitate attachment of the portable touch fastener to the desired object and support of the medical tubing tethering device when secured to the first portion of the mating touch fastener carried by the proximal end of the tether.

13. A medical tubing tethering device comprising:

a tether having a first proximal end and an opposed distal end;

a first attachment means being supported adjacent the proximal end of the tether for securing the medical tubing tethering device to a desired object;

the distal end of the tether having a second attachment means for coupling a medical tube thereto to facilitate support of the medical tube once the medical tubing tethering device is supported by the desired object;

wherein the first attachment means is a clip supported adjacent the proximal end portion of the tether; the clip is normally biased into a closed clamping position; and clip is manufactured from stainless steel and the tether is manufactured from a plastic material; and the medical tubing tethering device is used in combination with an anchor, and the anchor is provided with an attachment tab for coupling to the clip of the medical tubing tethering device and a remote surface of the anchor is provided with a pressure sensitive adhesive for securing the anchor to a desired object.

14. The medical tubing tethering device according to claim 13, wherein the anchor is a substantially flexible Y-shaped member which has two opposed legs and at least one the two opposed legs, on a surface opposite that supporting the attachment tab, supports the pressure sensitive adhesive.

15. The medical tubing tethering device according to claim 14, wherein a release liner covers the pressure sensitive adhesive of the anchor and the release liner is removable to expose the pressure sensitive adhesive of the anchor to facilitate securing of the anchor to a desired object.

16. A method of securing medical tubing with a tethering device, the method comprising the steps of:

providing a tether with a first proximal end and an opposed distal end;

supporting first attachment mechanism adjacent the proximal end of the tether for securing the medical tubing tethering device to a desired object;

providing the distal end of the tether with second attachment mechanism for coupling a medical tube thereto to facilitate support of the medical tube once the medical tubing tethering device is supported by the desired object; the distal end portion of the tether being a substantially helically shaped configuration with the substantially helically shaped configuration having an inherent resiliency for maintaining the distal end portion of the tether in its substantially helically shaped configuration, and the inherent resiliency of the distal end portion of the tether facilitates wrapping a portion of the substantially helically shaped configuration about a circumference of a medical tube to facilitate releaseable attachment of the medical tube to the distal end portion of the tether;

coupling the distal end of the tether, via the second attachment mechanism, to a medical tube; and securing the first attachment mechanism to a desired object.

17. The medical tubing tethering device according to claim 16, further comprising the step of forming the substantially helically shaped configuration of the distal end portion of the tether with a diameter which is smaller than an exterior diameter of the medical tube to be supported to provide a compressive retention force to the medical tube and facilitate retention thereof solely via use of the medical tubing tethering device.

18. The medical tubing tethering device according to claim 16, further comprising the step of forming a gap between each pair of adjacent wraps of the substantially helically shaped configuration of the distal end portion of the tether, and spacing the gaps equally along the substantially helically shaped configuration of the distal end portion of the tether.

19. The medical tubing tethering device according to claim 18, further comprising the step of solely using the inherent resiliency of a plurality of wraps of the substantially helically shaped configuration of the distal end portion of the tether to retain the medical tube.

20. The medical tubing tethering device according to claim 16, further comprising the step of forming a gap between each pair of adjacent wraps of the substantially helically shaped configuration of the distal end portion of the tether, and spacing the gaps equally along the substantially helically shaped configuration of the distal end portion of the tether; and solely using the inherent resiliency of the substantially helically shaped configuration of the distal end portion of the tether to retain the medical tube.

* * * * *